United States Patent [19]

Palumbo

[11] Patent Number: 4,495,942
[45] Date of Patent: Jan. 29, 1985

[54] DYNAMIC ANKLE BRACE

[76] Inventor: Pasquale M. Palumbo, 906 Frome La., McLean, Va. 22101

[21] Appl. No.: 575,532

[22] Filed: Jan. 31, 1984

Related U.S. Application Data

[63] Continuation of Ser. No. 327,706, Dec. 4, 1981, abandoned.

[51] Int. Cl.³ .............................................. A61F 3/00
[52] U.S. Cl. .................................................. 128/80 H
[58] Field of Search ................ 128/80 H, 80 R, 80 D, 128/80 C, 166

[56] References Cited

U.S. PATENT DOCUMENTS

| 459,616 | 9/1891 | Rohonczy | 128/80 H |
| 3,506,000 | 4/1970 | Baker | 128/80 R |
| 4,296,744 | 10/1981 | Palumbo | 128/80 C |

FOREIGN PATENT DOCUMENTS

| 635094 | 9/1936 | Fed. Rep. of Germany | ... 128/80 H |
| 696697 | 9/1940 | Fed. Rep. of Germany | ... 128/80 H |

Primary Examiner—John D. Yasko
Assistant Examiner—C. W. Shedd
Attorney, Agent, or Firm—Stevens, Davis, Miller & Mosher

[57] ABSTRACT

A dynamic ankle brace which includes a U-shaped felt pad contoured to fit about the lateral malleolus of the ankle and an elastic strap member connected to the U-shaped pad and adapted to be wrapped about the foot and ankle to apply pressure to the pad and ankle and to maintain the ankle and foot in a position of stability. The ankle brace may be used to replace conventional taping of the ankle to prevent ankle sprains, or for therapeutic purposes to provide stability and offer compression to diminish swelling after removal of a plaster cast or after surgery on the foot or ankle.

10 Claims, 9 Drawing Figures

DYNAMIC ANKLE BRACE

This application is a continuation of application Ser. No. 06/327,706, filed Dec. 4, 1981, now abandoned.

BACKGROUND OF THE INVENTION

This invention relates to stabilizing ankle braces or wraps and, in particular, to a new dynamic ankle brace which includes a U-shaped pad member and an elongated elastic strap member connected to the U-shaped pad and adapted to be wrapped in a predetermined manner about the ankle and foot of the user when the brace is in use to apply pressure to the pad and the ankle and foot and to provide stability.

The need for effective ankle braces and wraps has been well recognized in the fields of sports medicine, orthopedic surgery, and athletics for many years. Ankle wraps in the form of taping of the ankle to prevent ankle sprains have been commonly used by athletes for years. Physicians and surgeons have also recognized for many years the desirability of an effective ankle brace for post operative use or for use after removal of a plaster cast from the foot or ankle.

Others have proposed various ankle support or brace devices in an attempt to replace the traditional taping used by athletes whereby a web bandage and adhesive tape are utilized to wrap and tape an ankle. For example, Castiglia, U.S. Pat. No. 4,085,746, discloses an ankle wrap intended to provide effective bracing of an ankle and to replace conventional taping such as used by athletes.

SUMMARY OF THE INVENTION

Accordingly, an object of the present invention is to provide a dynamic ankle brace which improves on prior art ankle braces and is adapted to function dynamically, i.e. when the ankle and foot of the user are subject to motion when the brace is being worn by the user.

Another object of the invention is to provide an ankle brace having padded means associated therewith to fit about the lateral malleolus and to constrain the ankle to its position of greatest stability, thereby assisting in the prevention of ankle sprains.

A further object of the invention is to provide a dynamic ankle brace suitable for use by physicians, or surgeons, therapeutically, for example, after removal of a plaster or other cast of the foot or ankle, or after surgery of the ankle, to reduce swelling and to protect the lateral and/or medial ligaments of the ankle while healing and while the associated muscles are becoming rehabilitated.

A still further object of the invention is to provide an ankle brace which can be used to avoid the need for time-consuming and expensive manual taping of an ankle.

A still further object of the invention is to provide an ankle brace which is relatively simple and easy to put in place and which will provide effective ankle bracing without need for constant adjustment or readjustment by the user.

A still further object of the invention is to provide an ankle brace which can be utilized with minimial discomfort to the user and which remains effective during athletic activities.

A still further object of the invention is to provide an ankle brace having a relatively simple construction and which is relatively simple to manufacture.

Toward the fulfillment of these and other objects, the present invention includes a U-shaped pad adapted to fit about the lateral malleolus of the ankle when the brace is in use, with the lower portion of the "U" of said pad below the lateral maleolus of the ankle when the foot is in, for example, a normal standing position on a level surface, when the brace is in use, an elastic strap connected to said U-shaped pad and adapted to be wrapped about the ankle and foot of the user in a predetermined manner to apply force against said U-shaped pad when the brace is in use and means operably associated with said elastic strap for releasably holding said elastic strap in a wrapped position when the brace is in use. Preferably, the U-shaped pad is attached to an elastic sleeve adapted to have the ankle position substantially within said said sleeve when the brace is in use. In use, the brace functions to apply pressure to stabilize the ankle to prevent ankle sprains, to reduce swelling of the ankle, thereby promoting healing, and to promote comfort of the ankle.

DESCRIPTION OF THE PREFERRED EMBODIMENTS

The dynamic ankle brace of the present invention in its application by a user is shown in perspective view in FIGS. 6-9 as noted. The specific components parts and elements for one embodiment are shown in detail in FIGS. 1-5.

Figure 1:
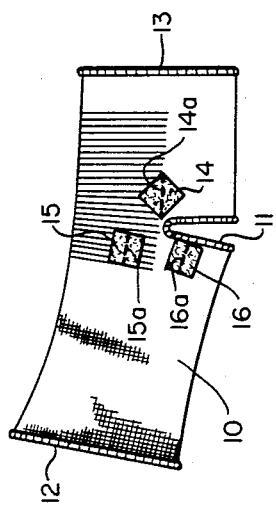
Figure 5:
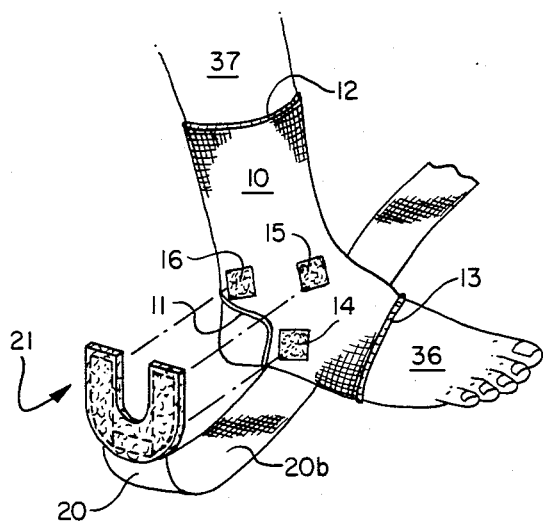
FIG. 5 is a perspective view illustrating the attachment of the elastic sleeve apparatus to the U-shaped pad and elastic strap apparatus of the present invention in one embodiment.

As shown in FIGS. 1 and 5, the dynamic ankle brace according to the present invention includes a tubular elastic or elastomer sleeve member 10 having an upper edge 12 and a lower edge 13 and a cutout or aperture therein 11. In use, the elastic sleeve 10 is adapted to have the foot and ankle of the user of the brace positioned substantially therein with the heel of the foot of the user in registration with the aperture or opening 11 as shown in FIG. 5. When the brace is in use, the front portion of the foot 36 extends out through the lower opening 13 of the sleeve 10 and the lower leg 37 extends into the sleeve 10 through the upper opening 12 as shown in FIG. 5.

Figure 2:
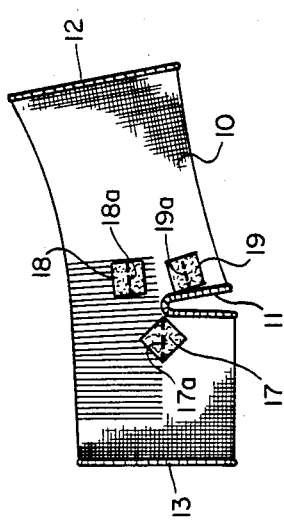
FIGS. 1 and 2 are elevation views of opposite sides, respectively, of the elastic sleeve apparatus of the present invention in one embodiment.

The sleeve and apparatus shown in FIG. 1 is illustrated in use in FIGS. 5-9 as noted, and the apparatus depicted in FIG. 1 is adapted for use in the embodiment illustrated for the right foot and ankle of a user. FIG. 2, in constrast to FIG. 1, shows the opposite side of the elastic sleeve member 10 from that shown in FIG. 1, and is adapted for use on the left foot and ankle (not shown) of a user.

As shown in FIG. 1, the elastic sleeve 10 includes thereon three Velcro strip means, 14, 15 and 16 which are attached to the outer surface of the sleeve 10 for example, by stitching means 14a, 15a and 16a, respectively, as shown. Similarly, the other side of the elastic sleeve 10 of FIG. 1, as illustrated in FIG. 2 similarly includes three Velcro strip means 17, 18, 19 attached to the outer surface of the sleeve 10 by, for example, stitching 17a, 18a, and 19a, as shown in FIG. 2. It is to be noted that in alternative embodiments (not shown) different numbers of these Velcro strip fastening means can be used. In the embodiment of the present invention illustrated in FIGS. 1–5, these respective sets of Velcro strip means, i.e. the first set of Velcro strip means 14, 15, and 16, and the second set of Velcro strip means 17, 18, and 19, are adapted to cooperate, alternately, with other elements of the dynamic ankle brace to permit the single elastic sleeve 10 as shown in FIGS. 1 and 2 to be used either for a right foot and ankle or a left foot and ankle of a user as will be explained.

Figure 3:
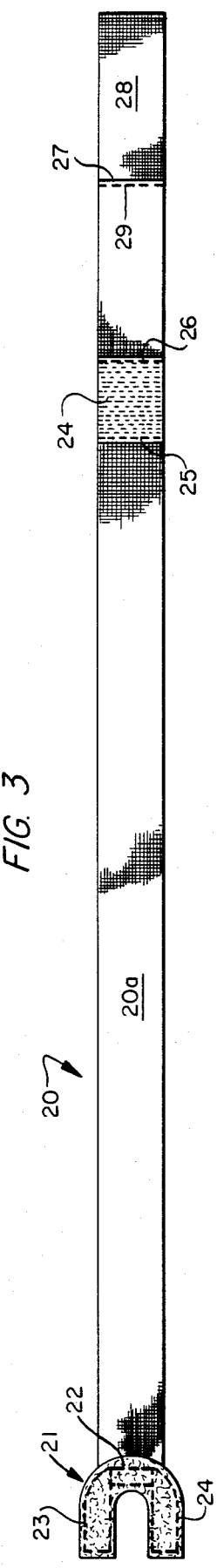
FIGS. 3 and 4 are front and rear plan views, respectively, of the U-shaped pad and elastic strap apparatus of the present invention in one embodiment.
Figure 4:
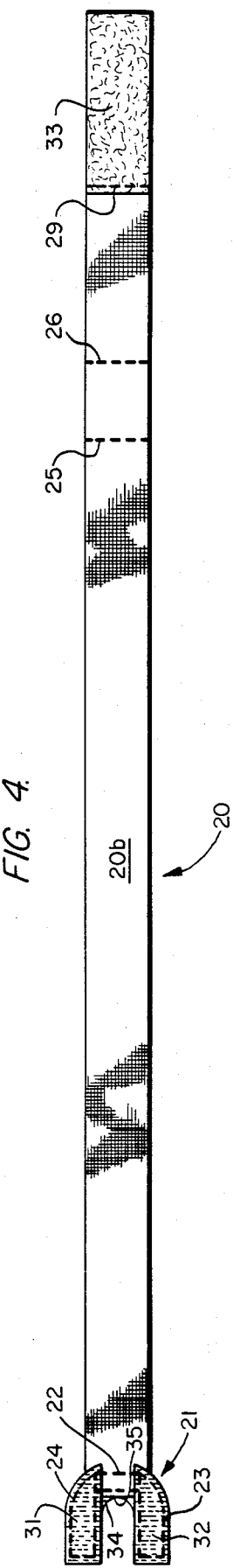

As shown in FIGS. 3, 4, and 5 the dynamic ankle brace of the present invention also includes a U-shaped pad 21 connected to an elastic strap member 20 having a first side 20a and a second side 20b as shown. The U-shaped pad member itself is preferably made of a material such as a felt pad or other resilient padding material and is fastened at the bottom of the "U" portion of the pad to a first end 35 of the strap member 20 by stitching 22 as shown in FIGS. 3 and 4.

In the embodiment illustrated in FIGS. 1–5, Velcro strip means 31 and 32 are disposed on portions of one surface of the U-shaped felt pad means 21 as shown in FIG. 4 and are attached thereto by, for example, additional stitching 23, 24 as shown in FIGS. 3 and 4. These Velcro strip means 31, 32, are selected to be usable to releasably engage, alternately, with the first set of Velcro strip means 14, 15, 16 or the second set of Velcro strip means 17, 18, 19 disposed on the respective opposite sides of the elastic sleeve 10 so that the combination of the U-shaped pad member 21 and the elastic arm member 20 may be releasably attached to either the first set (14, 15, 16) or the second set (17, 18, 19) of a fastening means asssociated with the elastic sleeve 10 when the brace is use, depending upon whether the ankle brace is to be used on a right foot or a left foot.

In an alternative embodiment (not shown), it is possible simply not to use the first set (14, 15, 16) or second set (17, 18, 19) of Velcro strip means associated with the elastic sleeve 10 and also not to use Velcro strip means 31, 32, associated with the U-shaped pad means 21. In lieu thereof, one may simply attach by appropriate means, such as stitching (not shown), the U-shaped pad 21 connected to the elastic arm member 20 directly to the outer surface of the sleeve 10. In this alternative embodiment, the U-shaped pad member 21 and the elastic strap member 20 are permanently attached to the elastic sleeve 10, and the use of a given ankle brace would, of necessity, be confined to either a right ankle and foot, or a left ankle and foot, depending upon the specific manufacture, for reasons which will be explained.

With this alternative embodiment (not shown), the user does not have to involve himself with the step of aligning and fastening the U-shaped member 21 to the elastic sleeve 10 when applying the ankle brace such as shown in FIG. 5 because the U-shaped member is permanently attached to the elastic sleeve 10. With this alternative embodiment, however, the user must be careful to use a given brace only on the right ankle and foot or on the left ankle and foot, depending upon the manufacture of the specific brace. In practice, many users of the ankle brace of this invention would, in fact, only need a single brace, i.e. only a brace for the right ankle and foot or only a brace for the left ankle and foot. Alternatively, many users would need two different braces, i.e. one for each ankle and foot. In either such case, it would be satisfactory, if not preferable, from the user's perspective to have the U-shaped padded member 21 permanently affixed to the sleeve member 10 rather than releasably attachable thereto.

As also shown in FIG. 4, the method of attachment of one end 35 of the elastic strap member 20 to the U-shaped pad member 21 is such that a first surface thereof 20a is in contact with a portion of a surface 34 of the U-shaped pad 21, and thereby achieves an attachment therebetween by connection over a region of the respective surfaces of each element.

The elastic strap member 20 also includes on the first surface 20a thereof, a Velcro strip means 24 attached thereto by stitching 25, 26 as shown in FIGS. 3 and 4. Preferably, the Velcro strip means 24 is attached to the elastic strap member 20 when it is not under tension such that the elastic strap member 20 may thereafter be stretched between the two lines of stitching attachment 25, 26 without being constrained by the inelastic Velcro strip means 24.

Another Velcro strip means 28 is attached as a tab, for example, by stitching means 29 as shown in FIGS. 3 and 4, at the second end 27 of the elastic strap member 20. This Velcro strip means 28 attached as a tab to the end 27 of the elastic strap member 20 includes an active Velcro attaching surface 33 on the side 20b of the strap member 20 which is adapted to be releasably attachable to the mating active Velcro strip surface of the Velcro strip means 24 previously described which faces outwardly from the opposite surface 20a of the elastic strap member 20.

In use, the foot and ankle of the user is first placed substantially within the elastic sleeve 10 with the heel of the foot of the user in registration with the opening 11 in the sleeve member 10 as shown in FIG. 5. Next, according to the embodiment of the invention illustrated in FIGS. 1 through 5, it is necessary for the user to attach the U-shaped pad member 21 to the elastic sleeve 10 by a cooperative engagement of the Velcro strips 16 and 31 and by cooperative engagement of the Velcro strips 14 and 15 with the Velcro strip 32 as shown. This attachment is effected so that the U-shaped pad fits about the end of the lateral malleolus (not explicitly shown) of the ankle.

As illustrated in FIG. 5, the attachment is effected so that the bottom portion of the "U" of the U-shaped pad will be positioned below the protruding end of the lateral malleolus when the U-shaped pad 21 is affixed to the elastic sleeve 10 and adjusted for use by the user.

In the alternative embodiment (not shown), in which the U-shaped pad member 21 is permanently attached to the elastic sleeve 10, it is only necessary for the user, when initially placing his foot and ankle substantially within the elastic sleeve 10 with his heel and registration with the opening 11, to initially adjust the positioning of the U-shaped pad to surround the front and back and lower portion of the protruding lateral malleolus of his ankle.

Figure 6:
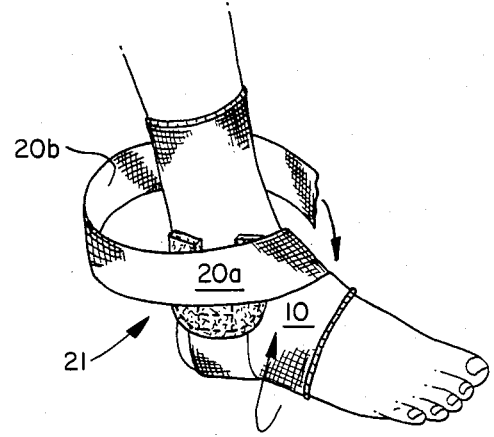
FIGS. 6 through 9 are perspective views illustrating the manner in which the dynamic ankle brace is wrapped about the foot and ankle of a user in accordance with the present invention.
Figure 7:
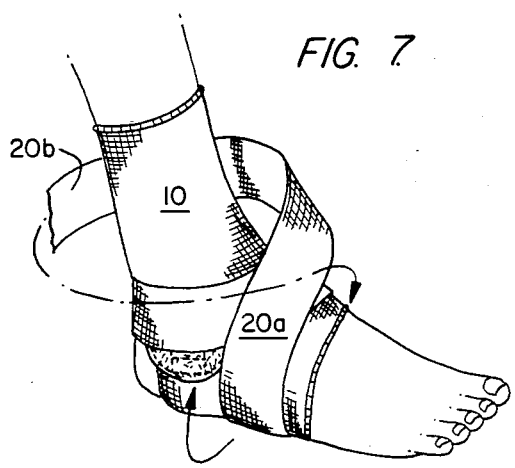
Figure 8:
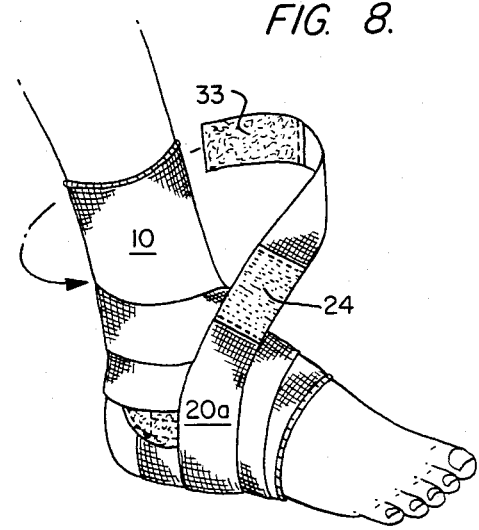

In either embodiment, once the foregoing steps have been accomplished, the user is then ready to effect the wrapping of the elastic strap 20 to affix the dynamic ankle brace in place and to apply appropriate and effective pressure therewith as illustrated in FIGS. 6 through 9, and as will be explained. The first step in wrapping the elastic strap 20 once the ankle and foot have been appropriately positioned within the elastic sleeve 10 and the U-shaped pad 21 has been appropriately positioned is to bring the second surface 20b of the elastic strap 20 underneath the foot and then upward and around and over the upper portion of the U-shaped pad 21 as shown in FIG. 6. Next, the second surface 20b of the elastic strap member is brought back behind the rear of the foot and lower leg and pressure is applied to the upper "U" portion of the U-shaped pad and the ankle by an appropriate tension adjustment to the elastic strap 20 as the wrapping continues. The elastic strap member 20 is then brought around forward towards the front of the foot but is then, again, brought under the foot, then up around the forward portion of the foot and then back around the rear portion of the lower leg as shown in FIGS. 6 and 7 as the wrapping continues. Next, the elastic strap member 20 is brought around from behind the rear portion of the lower leg, and is wrapped around, over and then under the forward portion of the foot as shown in FIGS. 7 and 8.

Figure 9:
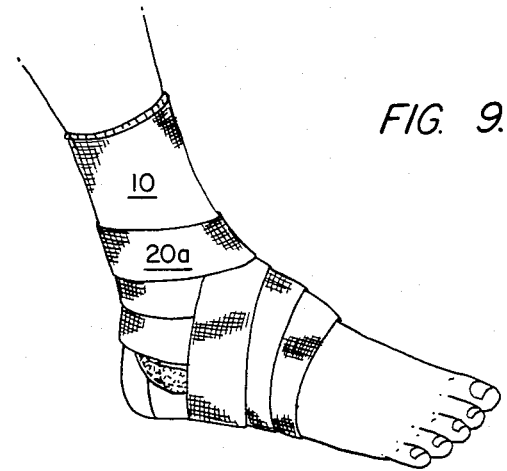

It is to be noted, that by the time the wrapping has been accomplished to the point shown in FIG. 8, the first Velcro strip means 24 on the surface 20a of the elastic strap 20 will be aligned approximately as shown in FIG. 8 ready to receive and cooperatively mate with the operatively associated Velcro strip tab 33 to releasably hold the dynamic ankle brace in the wrapped position at the conclusion of the final wrapping steps as shown in FIGS. 8 and 9. In the final wrapping steps, an appropriate tension adjustment is made to the strap member 20 to obtain effective positioning of the respective Velcro strip means 24 and 33 for the final cooperative engagement thereof so that the fully wrapped ankle brace will appear substantially as shown in FIG. 9.

It is thus seen that the U-shaped pad 21 of the ankle brace is first positioned about the protruding end of the lateral malleolus and is then securely wrapped in place using the elastic strap 20 attached thereto using a predetermined manner of wrapping. The elastic strap 20, when wrapped when the brace is in use, applies medially directed to pressure to the U-shaped pad 21, particularly to the upper "U" portion thereof, which, in turn, applies medially directed pressure to the lateral ligaments and soft tissues of the ankle.

Thus, it is seen, that the U-shaped pad 21 in cooperation with the other component elements of this ankle brace serves several functions. First, it permits the elastic strap member 20 to which it is attached to remain fixed firmly to the ankle, under conditions of dynamic movement of the foot and ankle, thereby preventing slippage of the ankle brace during normal motion and movement of the foot and ankle when the brace is in use. It, in effect, serves to anchor the elastic strap member 20. Secondly, the U-shaped pad member 21, due to its positioning on the foot and ankle when in use, applies medially directed pressure to the ankle components of the foot due to the force applied to the U-shaped pad member 21 by the wrapped elastic strap member 20. Those pressures and forces tend to stabilize positionally the ankle by placing the heel in the valgus position or a position of eversion stress, thereby tending to lock or constrain the ankle to its position of greatest stability. Thus the ankle brace functions to reduce or prevent the occurrence of ankle sprains. Thirdly, the positioning and the pressure forces applied to the ankle and foot by the combination of the U-shaped pad member and the wrapped elastic strap member 21 tends to apply pressure to the soft tissues about the lateral malleolus to reduce swelling and to protect the ligaments of the ankle, for example, while they are healing and while the associated muscles are becoming rehabilitated, following, for example, surgery on or removal of a plaster cast from the ankle or foot.

It is, of course, to be noted that it is necessary for the apparatus of the present invention to be manufactured in different sizes to accommodate persons having different sized ankles and feet.

Accordingly, it is seen that the dynamic ankle brace according to the present invention accomplishes the above described objects as well as other objects which will be apparent to those skilled in the art. It will be further apparent skilled in the art that various modifications and changes may be made to the present invention without departing from the scope of the invention as defined in the appended claims.

What is claimed is:

1. A dynamic ankle brace for bracing an ankle of a lower extremity comprising:
    a U-shaped pad means adapted to fit around the lateral malleolus of the ankle when said brace is in use for applying pressure to the area surrounding the lateral malleolus;
    an elastic strap means, having a first end connected to said U-shaped pad means and a second end, said elastic strap means adapted to be wrapped around the ankle and foot in a predetermined manner, for applying force against said U-shaped pad when said brace is in use; and
    means, operably associated with said elastic strap, for releasably holding said elastic strap in the wrapped position when said brace is in use.

2. A dynamic ankle brace according to claim 1 wherein said first end of said elastic strap is connected to said U-shaped pad means along the bottom portion of the "U" of said pad means.

3. A dynamic ankle brace according to claim 1 wherein said U-shaped pad means is adapted to fit around the lateral malleolus of the ankle such that bottom portion of the "U" of said pad means is below the lateral malleolus of the ankle when the foot is in a normal standing position on a level surface when the brace is in use.

4. A dynamic ankle brace according to claim 2 wherein a portion of a first surface of said U-shaped pad means is attached to a portion of a first surface of said elastic strap.

5. A dynamic ankle brace according to claims 1, 2, 3, or 4 further comprising an elastic sleeve adapted to be attached to said U-shaped pad means when the brace is in use, and adapted to have the ankle positioned substantially within said sleeve when the brace is in use.

6. A dynamic ankle brace according to claims 1, 2, 3, or 4 further comprising an elastic sleeve attached to said U-shaped pad and adapted to have the ankle positioned substantially within said sleeve when the brace is in use.

7. A dynamic ankle brace according to claims 1, 2, 3, or 4, wherein said elastic strap has at least a first surface and said means for releasably holding said elastic strap comprises first and second cooperating portions of a hook and pile fastener; said first portion of said hook and pile fastener being disposed along a portion of said first surface of said elastic strap, said second portion of said hook and pile fastener being attached as a tab at said second end of said elastic strap; said first and second portions of said hook and pile fastener adapted to be releasably connected to each other when the brace is in use.

8. A dynamic ankle brace according to claims 1, 2, 3, or 4 wherein said U-shaped pad means comprises a felt material.

9. A dynamic ankle brace for bracing an ankle and foot comprising:

a U-shaped pad means adapted to fit around the lateral malleolus of the ankle when the brace is in use for applying pressure surrounding said lateral malleolus;

an elastic strap means, connected to said U-shaped pad means and adapted to be wrapped around said ankle and foot in a predetermined manner, for applying force against said U-shaped pad means when the brace is in use;

means, operably associated with said elastic strap, for releasably holding said elastic strap in the wrapped position when the brace is in use;

an elastic sleeve means, to which said U-shaped pad means is adapted to be attached when the brace is in use, for enclosing said ankle substantially within said sleeve means when the brace is in use; and first attachment means, disposed on a first surface of said U-shaped pad, and second and third attachment means disposed, respectively, on opposite sides of the outer surface of said sleeve means, said first attachment means being adapted to function cooperatively, depending on whether or a right or left ankle is being braced, with either one of said second or third attachment means, when the brace is in use, to releasably attach said U-shaped pad means to said sleeve.

10. A dynamic ankle brace according to claim 9 wherein said first, second and third attachment means each comprises a portion of a hook and pile fastener.

* * * * *